(12) United States Patent
Teles et al.

(10) Patent No.: US 6,184,420 B1
(45) Date of Patent: Feb. 6, 2001

(54) PREPARATION OF UNSATURATED KETONES

(75) Inventors: Joaquim Henrique Teles, Altrip; Norbert Rieber, Mannheim; Klaus Breuer, Altrip; Dirk Demuth, Mannheim; Hartmut Hibst, Schriesheim; Stefan Kaeshammer, Schifferstadt; Heinz Etzrodt, Neustadt; Wulf Kaiser, Bad Duerkheim, all of (DE)

(73) Assignee: BASF Aktiengesellschaft, Ludwigshafen (DE)

( * ) Notice: Under 35 U.S.C. 154(b), the term of this patent shall be extended for 0 days.

(21) Appl. No.: 09/150,925

(22) Filed: Sep. 10, 1998

(30) Foreign Application Priority Data

Sep. 10, 1997 (DE) .............................. 197 39 716

(51) Int. Cl.⁷ .............................. C07C 49/203

(52) U.S. Cl. .............. 568/405; 568/361; 568/408; 568/409; 568/415

(58) Field of Search ................. 568/691, 361, 568/405, 408, 409, 415; 502/77

(56) References Cited

U.S. PATENT DOCUMENTS

| | | | |
|---|---|---|---|
| 3,029,287 | 4/1962 | Marbet et al. | 260/587 |
| 3,453,317 | 7/1969 | Marbet et al. | 260/476 |
| 3,493,619 | 2/1970 | Marbet et al. | 260/601 |
| 5,576,465 | 11/1996 | Kaufhold | 568/691 |
| 5,767,325 | 6/1998 | Schroeder et al. | 568/691 |

FOREIGN PATENT DOCUMENTS

| | | |
|---|---|---|
| 1 193 490 | 2/1966 | (DE) . |
| 195 44 450 | 6/1997 | (DE) . |
| 196 49 564 | 6/1998 | (DE) . |
| 197 26 667 | 12/1998 | (DE) . |
| 0 165 647 | 12/1985 | (EP) . |
| 0 299 286 | 1/1989 | (EP) . |
| 0 703 211 | 3/1996 | (EP) . |
| 0 776 879 | 6/1997 | (EP) . |
| 981702 | 1/1965 | (GB) . |
| WO 98/23570 | 6/1998 | (WO) . |

OTHER PUBLICATIONS

G. Saucy et al., "Über Die Reaktion Von Tertiären Vinyl-carbinolen Mit Isopropenläther Eine Neue Mthode Zur Her Stellung Von γ, δ–Ungestätigten Ketonen", Helvetica Chimica Acta, vol. 50, pp. 2091–2100, 1967.

G. Saucy et al., "Über Eine Neuartige Synthese Von β–Ketonallenen Durch Reaktion Von Tertiären Acetylencarbinolen Mit Vinyläthern Eine Ergiebige Methode Zur Darstellung Des Pseudojonons Und Verwandter Verbindungen", Helvetica Chimica Acta, vol. 50, pp. 1158–1167, 1967.

(List continued on next page.)

*Primary Examiner*—Sreeni Padmanabhan
(74) *Attorney, Agent, or Firm*—Oblon, Spivak, McClelland, Maier & Neustadt, P.C.

(57) ABSTRACT

Unsaturated ketones of the formulae Ia and Ib

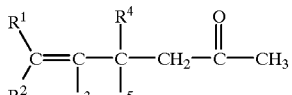

Ia

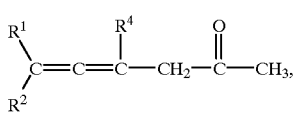

Ib are prepared by a process consisting of the combination of the following reactions:

a) The conventional reaction of an allyl alcohol of the formula IIa or a propargyl alcohol of the formula IIb

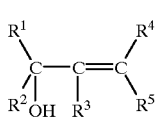

IIa

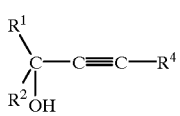

IIb with an isopropenyl ether of the formula III

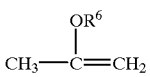

III with formation of a ketal of the formula IV

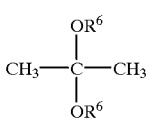

IV as a byproduct, b) preparation of the isopropenyl ether of the formula III by reacting a ketal of the formula IV with propyne or allene, or a mixture thereof in the gas phase at elevated temperatures in the presence of a heterogeneous catalyst containing zinc or cadmium together with silicon or oxygen, and c) feeding the ketal of the formula IV formed in the reaction (a) into stage (b) for the preparation of the isopropenyl ether of the formula III again.

9 Claims, 1 Drawing Sheet

OTHER PUBLICATIONS

A.G. Merkulov et al., "Formation Mechanism of Zinc Silicates", Tr. Soveshch. Eksp. Tekh. Mineral. Petrogr., vol. 8, pp. 332–328, 1971 (with English Abstract).

A.G. Merkulov et al., "Low–Temperature Synthesis of Zinc Silicates", Izv. Sib. Otd. Akad. Nauk SSSR, Ser. Khim. Nauk, vol. 4, pp. 70–74, 1969 (with English Abstract).

T. Baird et al., "An IR and EM Study of the Reactivity of Some Divalent Metal Hydroxides with Silica Gel", Reactivity of Solids, Proce. Int. Sympos., vol. 8, pp. 337–342, 1977.

H. Nagata et al., "Analytical Study of the Formation Process of Hemimorphite–Part I–Analysis of the Crystallization Process by the Co–Precipitation Method", Zairyo–to–Kankyo, vol. 42, pp. 225–233, 1993.

D.M. Roy et al, "Stability of Minerals in the System $ZnO-SiO_2-H_2O^1$", Econ. Geol., vol. 51, pp. 432–443, 1956.

P. Taylor et al., "Hydrothermal Synthesis of Zinc Silicates From Borosilicate Glasses and From Mixtures of Zinc Oxide and Silica", Polyhedron, vol. 3, No. 2, pp. 151–155, 1984.

Chemical Abstracts, vol. 112, No. 7, Feb. 12, 1990, Abstract No. 54986a, O.N. Temkin et al, "A Catalyst for the Manufacture of Methyl and Ethyl Isopropenhyl Ethers".

Chemical Abstracts, vol. 112, No. 7, Feb. 12, 1990, Abstract No. 54987b, O.N. Temkin et al., "A Catalyst for the Manufacture of Methyl and Ethyl Isopropenyl Ether".

PREPARATION OF UNSATURATED KETONES

The present invention relates to the preparation of γ,δ-monounsaturated or β,γ,δ-diunsaturated ketones which are useful fragrances or useful intermediates for the synthesis of natural substances, by the combination of conventional reactions of allyl alcohols or propargyl alcohols with isopropenyl ethers with the formation of ketals of acetone as a byproduct, the isopropenyl ethers being prepared by reacting ketals of acetone with propyne or allene in the gas phase over heterogeneous catalysts and the ketal of acetone, obtained as byproduct, being fed into the stated preparation of the isopropenyl ether.

DE 1 193 490 and R. Marbet and G. Saucy, Helv. Chim. Acta 50, (1967), 2091–2095 and 2095–2100 disclose a process for the preparation of γ,δ-unsaturated ketones by reacting an allyl alcohol with enol ethers, in particular isopropenyl ethers, in the presence of an acid catalyst, e.g. phosphoric acid.

Furthermore, U.S. Pat. No. 3,029,287 and G. Saucy and R. Marbet, Helv. Chim. Acta 50, (1967) 1158–1167 disclose the reaction of the propargyl alcohols with enol ethers in the presence of acid catalysts to give β,γ,δ-diunsaturated ketones.

In both reactions, one mole of the corresponding ketal is formed as a byproduct from 2 moles of enol ether used, for example acetone dimethyl ketal from isopropenyl methyl ether used, in accordance with the following equations:

Equation 1

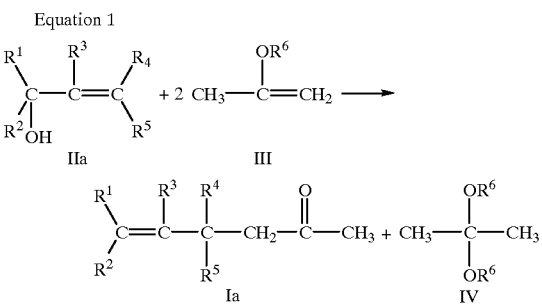

Equation 2

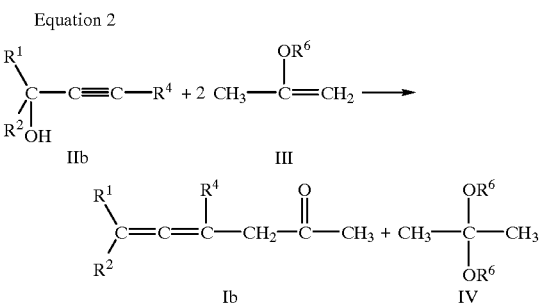

In these equations, $R^1$ to $R^5$ are each hydrogen or alkyl, alkenyl, cycloalkyl, cycloalkenyl, aryl or aralkyl radicals which are unsubstituted or substituted by oxygen-containing groups, it also being possible for $R^1$ and $R^2$ together with the carbon atom to which they are bonded, to form a 5- or 6-membered ring, and $R^6$ is alkyl of 1 to 4 carbon atoms.

The ketal IV obtained as a byproduct must be converted back into the enol ether III for economic reasons. It is known that this can be done by converting the ketals, either in the liquid phase with acidic catalysts (according to EP 703 211) or in the gas phase over heterogeneous catalysts (according to DE 19 544 450) with elimination of alcohol, into the corresponding enol ethers according to the following equation:

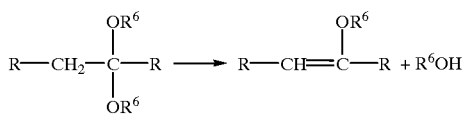

Here, R is hydrogen or alkyl and $R^6$ has the abovementioned meaning.

The stated known processes permit the preparation of the enol ethers in good yields in some cases but have the following disadvantages:

The reaction in the liquid phase according to EP 703 211 requires the use of a dissolved foreign substance, ie. an organic acid, the removal of which from the reaction mixture requires an additional separation step. Compared with the process in the liquid phase using a homogeneously dissolved catalyst, the process according to DE 19544450 has the advantage of the reaction in the gas phase over a heterogeneous catalyst that requires fairly high temperatures.

Common to both processes is that one mole of alcohol is separated per mole of ketal and has to be separated off in an additional purification step, at considerable expense in some cases, and as a rule has to be discarded. This applies in particular to methanol, which frequently forms azeotropic mixtures. The weight yield, based on the ketal, is thus inevitably reduced.

It is an object of the present invention to provide a combination process which on the one hand permits the preparation of the required enol ether III over a heterogeneous catalyst in good yields without the alcohol originating from the ketal being obtained as a byproduct in stoichiometric amount and, on the other hand, recycling of the ketal obtained in the reactions of equations 1 and 2 into the preparation of the enol ethers.

We have found that this object is achieved, according to the invention, by a process for the preparation of unsaturated ketones of the formulae Ia and Ib

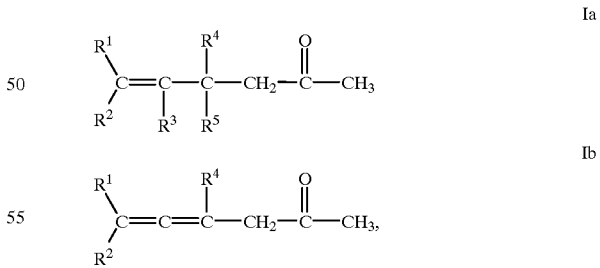

where $R^1$, $R^2$, $R^3$, $R^4$ and $R^5$ are each hydrogen or alkyl, alkenyl, cycloalkyl, cycloalkenyl, aryl or aralkyl radicals which are substituted or unsubstituted by oxygen-containing groups, it also being possible for $R^1$ and $R^2$ together to form a 5- or 6-membered ring, which comprises the combination of the following reactions:

a) The conventional reaction of an allyl alcohol of the formula IIa or a propargyl alcohol of the formula IIb

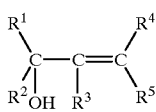
                           IIa

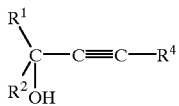
                           IIb with an isopropenyl ether of the formula III

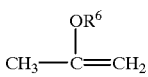
                           III where $R^6$ is alkyl having 1 to 4 carbon atoms, with formation of a ketal of the formula IV

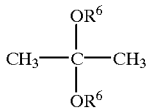
                           IV where $R^6$ has the abovementioned meaning, as a byproduct,
   b) preparation of the isopropenyl ether of the formula III by reacting a ketal of the formula IV with propyne or allene, or a mixture thereof in the gas phase at elevated temperatures in the presence of a heterogeneous catalyst containing zinc or cadmium together with silicon or oxygen, and
   c) feeding the ketal of the formula iv formed in the reaction (a) into stage (b) for the preparation of the isopropenyl ether of the formula III again.

The reaction of stage (a) is described in detail in the technical literature and is claimed in the present invention not for itself, but in combination with steps (b) and (c):

The conditions in stage (a) are described in DE 1193490 or U.S. Pat. No. 3,029 287 or the stated publications in Helv. Chim. Acta. In this context, the information in these patent publications and literature publications are hereby expressly incorporated by reference.

The conditions in stage (a) are in general not critical for carrying out the novel combination process and can of course also be varied, for example by the choice of the catalyst and, if required, of the starting materials.

Accordingly, more recent improvements of the reaction in stage (a) are of course also suitable, as described, for example, in DE 19 649 564.4.

Preferred starting materials of the formula IIa are in particular tertiary allyl alcohols, $R^1$ preferably being a saturated or unsaturated, branched or straight-chain alkyl radical which is unsubstituted or substituted by oxygen-containing groups, e.g. methoxy or ethoxy groups, an aryl radical or an alkylaryl radical of up to 20 carbon atoms and $R^2$ is preferably $C_1$–$C_4$-alkyl, in particular methyl, it also being possible for $R^1$ and $R^2$ together to be tetramethylene or pentamethylene which is unsubstituted or substituted by one or more lower alkyl groups, and $R^3$, $R^4$ and $R^5$ are each hydrogen.

Specific examples are 3-methyl-1-buten-3-ol, 3,7-dimethyl-1-octen-3-ol (hydrolinalool), 3,7-dimethylocta-2,6-dien-3-ol (linalool), 1-vinylcyclohexanol, 3,7,11-trimethyl-dodeca-1,6,10-trien-3-ol (nerolidol), 3,7,11-trimethyl-dodeca-1,6-dien-3-ol (hydronerolidol) and 3,7,11-trimethyl-dodec-1-en-3-ol(tetrahydronerolidol) and isophytol.

Preferred propargyl alcohols are tertiary propargyl alcohols of the formula IIb where $R^1$ is a saturated or unsaturated, branched or straight-chain alkyl radical which is unsubstituted or substituted by oxygen-containing groups, or an aryl radical or an alkylaryl radical, each of up to 20 carbon atoms, and $R^2$ is $C_1$–$C_4$-alkyl, in particular methyl, it also being possible for $R^1$ and $R^2$ together to be tetramethylene or pentamethylene which is unsubstituted or substituted by one or more lower alkyl groups, and $R^4$ is hydrogen.

Specific examples are 3-methylbutyn-3-ol, 3,7-dimethyl-1-octyn-3-ol(hydrodehydrolinalool), 3,7-dimethylocta-6-en-1-yn-3-ol(dehydrolinalool), 3,7,11-trimethyldodeca-6,10-dien-1-yn-3-ol(dehydronerolidol), 3,7,11-trimethyldodeca-6-en-1-yn-3-ol and 3,7,11-trimethyldodec-1-yn-3-ol.

A particularly suitable isopropenyl ether of the formula III is isopropenyl methyl ether.

The preparation of the isopropenyl ethers of the formula III

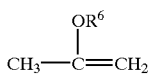
                           III where $R^6$ has the abovementioned meanings, as described more comprehensively and claimed in German Patent Application 19 726 667.3, is carried out according to stage (b) by reacting a ketal of the formula IV

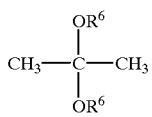
                           IV with propyne and/or allene in the gas phase in the presence of a heterogeneous catalyst containing zinc or cadmium and silicon and oxygen.

Although the mechanism of this reaction is not known in detail, the reaction may be regarded formally as if one mole of an alcohol $R^6OH$ is transferred from the dialkoxy compound of the formula IV to the acetylene or allene with formation of the enol ether of the formula III.

Examples of suitable ketals are the dimethyl, diethyl, di-n-propyl, di-n-butyl and diisobutyl ketals of acetone. 2,2-Dimethoxypropane (acetone dimethyl ketal) is particularly preferred as a starting material.

The ketals and their preparation from acetone are disclosed in the technical literature. They are obtained, for example, by reacting acetone with the corresponding alcohols or preferably by an addition reaction of alcohols with alkynes or allene, mixtures of enol ethers and the corresponding ketals being obtained, enol ethers being used immediately after the separation of said mixtures and it being possible to feed the ketals to stage (b).

In the overall balance of the novel process, however, only the losses of ketal as a result of secondary reactions should be replenished since, in the overall balance according to Equations 3 and 4 and Summation equation 5, the required enol ether is constantly formed again from propyne and allene.

Equation 3 (for the reaction of the allyl alcohols as in the Example)

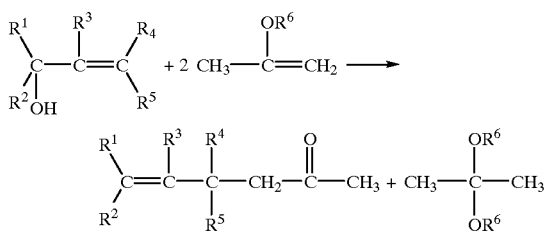

Equation 4

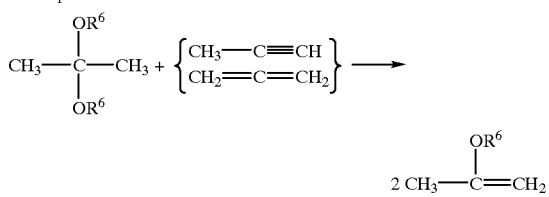

Equation 5

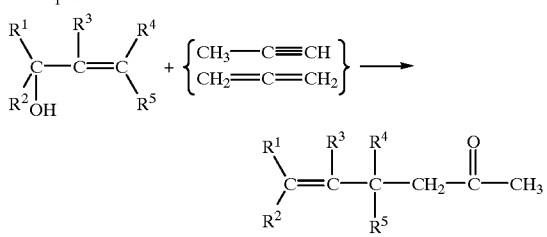

Instead of pure methylacetylene or pure allene, mixtures thereof may also be used, especially mixtures as can be isolated, for example, from a C$_3$ stream of a steamcracker.

The reaction of the ketals or acetals with the acetylenes or allenes is carried out in the presence of the heterogeneous catalyst containing zinc or cadmium and silicon and oxygen in the gas phase, either over a fixed bed or in a fluidized bed at from 50 to 400° C., preferably from 100 to 250° C., particularly preferably from 120 to 200° C., and pressures of from 0.1 to 50, in particular from 0.8 to 20, particularly preferably from 0.9 to 10, bar (all pressures are based on the sum of partial pressures of the starting materials).

If required, the reaction mixture may be diluted with inert gases, such as nitrogen, argon, low molecular weight alkanes or olefins for operational safety or better heat removal.

The molar ratio of ketal or acetal to alkyne or allene may be from 0.01 to 100, and is preferably from 0.1 to 2, particularly preferably from 0.7 to 1.3.

Suitable catalysts containing zinc or cadmium and silicon and oxygen are cadmium silicates and preferably zinc silicates, for example silicates selected from the group consisting of (a) X-ray amorphous zinc silicate and cadmium silicate, prepared by impregnating a silica carrier with a zinc or cadmium salt, (b) crystalline zinc silicate having essentially the composition and structure of hemimorphite of the formula Zn$_4$Si$_2$O$_7$(OH)$_2$·H$_2$O, where the zinc may be present in up to 25% more or less than the stoichiometric amount, and/or (c) essentially X-ray amorphous zinc silicate, prepared by precipitation in aqueous solution from a soluble silicon and zinc compound of the formula V

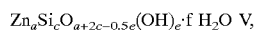

$Zn_aSi_cO_{a+2c-0.5e}(OH)_e \cdot f\ H_2O$  V, where e is from 0 to 2a+4c, the ratio a/c is from 1 to 3.5 and the ratio f/a is from 0 to 200.

(a) X-ray amorphous zinc silicate or cadmium silicate catalysts are obtained, for example, by loading amorphous silica with a zinc salt or cadmium salt and forming the catalyst by thermal treatment.

The SiO$_2$ carrier is at least predominantly amorphous, has a BET surface area from 10 to 1500 m$^2$/g, particularly preferably from 100 to 500 m$^2$/g and water absorbtivity of from 0.1 to 2, particularly preferably from 0.7 to 1.3 ml/g and can be used in the form of a powder or in the form of prepared moldings. The carrier can furthermore be calcined prior to impregnation. Preferably, however, the carrier is not calcined.

The zinc or cadmium compound used is a compound which is soluble in a suitable solvent. Zinc(II) salts which are soluble in water or aqueous ammonia or alcohols, preferably lower alcohols, and whose decomposition temperature is below 400° C. to 500° C. are preferably used.

An ammoniacal zinc(II) acetate solution is particularly preferably used for the impregnation. In some cases, it has proven advantageous to carry out the loading with zinc in a plurality of successive impregnations.

If the carrier is used in the form of a powder, the catalyst may be brought into the desired form by shaping (for example mixing, kneading and extrusion or pelleting).

To increase the pore volume, pore formers may also be used during the shaping (for example superabsorbers, such as Lutexal® (from BASF Ludwigshafen) or Walocel® (methylcellulose/synthetic resin combination, from Wolff, Walsrode)).

Alternatively, it is also possible to impregnate another carrier, eg. Al$_2$O$_3$, with a silica precursor compound (eg. Si(OR)$_4$) and with a zinc salt or cadmium salt.

The zinc or cadmium load may vary within wide limits. Typical values for an uncalcined precatalyst which was prepared by impregnating an SiO$_2$ carrier with a zinc salt or cadmium salt are, for example, from 1 to 60, preferably from 7 to 30, particularly preferably from 10 to 25, % by weight (calculated in each case as ZnO or CdO) of Zn or Cd. The precatalyst may furthermore be doped with other elements, preferably alkali metals, alkaline earth metals or transition metals. Moreover, the catalytically active component may be doped with up to 80, preferably up to 50, in particular up to 20, mol percent of further metals selected from the group (A) consisting of beryllium, magnesium, calcium, strontium, barium, manganese, iron, cobalt, nickel and copper and from the group (B) consisting of titanium, zirconium, hafnium, germanium, tin and lead, some of the elements of group (A) replacing zinc or cadmium and some of the elements from group (B) replacing silicon.

The precatalyst can then be calcined at not more than 600° C., in particular from 80 to 300° C., in air or under an inert gas. Calcination at from 120 to 250° C. in air is particularly preferred.

After the preparation of the generally still catalytically inactive precatalyst by application of a zinc or cadmium compound to a silica carrier, forming is preferably carried out, in which the actual active phase is formed in particular on the surface of the catalyst. This solid-state reaction is promoted by the presence of water, alcohols, preferably lower alcohols, or carboxylic acids, preferably lower carboxylic acids, and is therefore advantageously carried out by heating the precatalyst at from 50 to 400° C. in a water- or alcohol-containing atmosphere. The reaction is preferably carried out at from 100 to 250° C. in a water- or methanol-containing gas mixture. The reaction is particularly preferably carried out at from 120 to 200° C. with a methanol-containing gas mixture directly in the reactor in which the reaction with the alkyne or allene is subsequently to take place. If a precatalyst based on zinc acetate is used, it is very easy to determine when the solid-state reaction is complete as virtually no methyl acetate is to be found in the exit gas at this time. In some cases it has proven advantageous to treat the precatalyst under reaction conditions with a mixture of methanol with propyne and allene and possibly also other components (eg. propene or propane) for the formation of the active phase. Formation of the active layer is indicated by the increase in the propyne and allene conversion (after from about 5 to 30 minutes, depending on the temperature), by the increase in the selectivity (after from 10 to 300 minutes, depending on the temperature) and by the decline in the concentration of methyl acetate in the exit gas. A steady state (with high propyne or allene conversions) and a high selectivity is reached after from about 2 to 20 hours, depending on the temperature.

It is also possible to prepare the corresponding mercury silicates but these are technically and ecologically less suitable.

Standard methods were used for characterizing the catalyst samples (fresh samples as well as samples removed from the reactor). The measured BET surface area, which is typically from 10 to 800 m$^2$/g, and the hardness are stated in the respective examples. Catalysts having BET surface areas of from 100 to 400 m$^2$/g are preferred. Furthermore, the samples were investigated in detail by means of powder X-ray diffractometry (XRD) and transmission electron microscopy (TEM). Neither of the two structure analysis methods reveals any long-range order in the sense of a crystalline structure; all samples were amorphous. The distribution of the zinc over the carrier was investigated on appropriate sections under the electron microscope and by means of a microprobe. All samples, even after removal from the reactor, show that the catalyst has a substantially homogeneous distribution of elements and contains little or no crystalline ZnO. In the IR investigation (KBr pellets), the active catalyst prepared with zinc acetate shows no acetate bands (these are still visible in the precatalyst at 1570, 1410, 670 and 610 cm$^{-1}$). In the $^{13}$C-CP-MAS-NMR, too, acetate signals are no longer present. In the $^{29}$Si-CP-MAS-NMR, the catalyst shows only the broad band at −109 ppm which is typical of amorphous SiO$_2$, and a shoulder at −99 ppm (about 10% of the intensity of the main peak). The elemental analysis of a zinc acetate/SiO$_2$ precatalyst shows that the molar C/Zn ratio is dependent on the calcination temperature. Catalysts dried at room temperature have a C/Zn ratio of 3.5 −4. After calcination at 200–250° C. (optimum temperature), the C/Zn ratio is from 1 to 2. At higher temperatures, the C/Zn ratio decreases even further, as does the catalytic activity of the catalysts formed therefrom. After calcination at 500° C. (24 hours), the C/Zn ratio in the precatalyst is 0.02. Active catalyst cannot be formed from this. Since the decomposition of the zinc acetate on the precatalyst is relatively slow, said precatalyst can be exposed to even higher temperatures for short times without the catalytic activity being completely lost.

(b) Hemimorphite as catalyst

Hemimorphite is a zinc silicate of the formula Zn$_4$Si$_2$O$_7$(OH)$_2$·H$_2$O. However, not only pure hemimorphite but in general heterogeneous catalysts which contain, as active component, at least predominantly zinc silicate having the structure of hemimorphite of the formula Zn$_4$Si$_2$O$_7$(OH)$_{2-2y}$O$_y$·x H$_2$O, where x and y are from 0 to 1, are suitable for the novel reaction.

The preparation of hemimorphite is disclosed in the literature. It can be carried out under standard pressure conditions or under hydrothermal conditions.

(b1) Preparation under standard pressure conditions

A. G. Merkulov and B. S. Khristoforov, (Tr. Soveshch, Eksp. Tekh. Mineral. Petrogr., 8th (1971), Meeting Date 1968, 322–8; Editor(s): V. V. Lapin; Publisher: "Nauka", Moscow, USSR) describe the preparation of various zinc silicates by reaction of various zinc salts (carbonate, sulfate, chloride, acetate, oxide) with sodium silicate and sodium hydroxide in aqueous solution at 90–100° C. and at atmospheric pressure. Different zinc silicates form depending on the pH established. For example, pure sauconite having the composition Zn$_3$Si$_4$O$_{10}$(OH)$_2$·n H$_2$O forms at a final pH of 5–6. Pure willemite (α-Zn$_2$SiO$_4$) is obtained at a pH of 6.5–8.5. On the other hand, pure hemimorphite (Zn$_4$Si$_2$O$_7$(OH)$_2$·H$_2$O) crystallizes out only in a weakly alkaline medium at pH greater than 10.

In another paper by the stated authors (A. G. Merkulov and B. S. Khristoforov, Izv. Sib. Otd. Akad. Nauk SSSR, Ser. Khim. Nauk 4 (1969), 70–4), it is stated that pure hemimorphite is formed in the reaction of the zinc salts with sodium silicate and sodium hydroxide at 90–100° C. and atmospheric pressure in aqueous solution only at a pH of 10–12.

Furthermore, T. Baird, A. G. Cairns Smith and D. S. Snell (Reactivity of Solids, Proc. Int. Symp., 8th (1977), Gothenberg, Meeting Date 1976, 337–42; Editor(s): J. Wood, O. Lindqvist und C. Helgesson; Publisher: Plenum Press, New York, N.Y.) were able to prepare large crystals of hemimorphite by reacting Zn(OH)$_2$ with silica and LiOH in aqueous solution at a pH of 10.

Finally, H. Nagata, M. Matsunage and K. Hosokawa (Zairyo-to-Kankyo 42 (1993), 225–233) prepared hemimorphite by reacting aqueous zinc sulfate solution with sodium hydroxide solution and aqueous sodium silicate solution at a pH of 13, isolating the precipitate obtained and washing it thoroughly and ageing it at 85° C. for at least 24 hours.

(b2) Hydrothermal preparation

According to EP 165 647, hemimorphite can be prepared from an acid-treated clay mineral and zinc oxide or zinc hydroxide under hydrothermal conditions (170° C., 5 h). However, the acid pretreatment of the clay is very expensive and this process is therefore disadvantageous.

According to D. M. Roy and F. A. Mumpton (Econ. Geol. 51 (1956), 432–443), hemimorphite can also be obtained by a hydrothermal reaction of mixtures of ZnO and SiO$_2$ at 175–200° C. (composition: 3 ZnO+2 SiO$_2$). The product obtained contains predominantly hemimorphite but is contaminated with sauconite (Zn$_3$Si$_4$O$_{10}$O(OH)$_2$·4 H$_2$O).

Finally, P. Taylor and D. G. Owen, (Polyhedron 3(2) (1984), 151–155) describe the hydrothermal synthesis of hemimorphite by reacting ZnO with SiO$_2$ in aqueous solution at 150° C. However, long reaction times of at least 4 days are required for the preparation of products having a high hemimorphite content.

Although hemimorphite products obtained by the known methods described above are very suitable as a catalyst for the novel addition reaction, it was found to be desirable further to improve their properties to propose a method which permits the preparation of catalysts with a reproducibly good property profile.

Accordingly, a preferred novel preparation method, both under atmospheric pressure and under hydrothermal conditions, is one in which an alkali metal or alkaline earth metal silicate, preferably sodium silicate, is reacted with a zinc salt, in particular zinc nitrate, and a base, such as an alkali metal or alkaline earth metal hydroxide, in particular sodium hydroxide, in aqueous solution at pH of from 4 to 9.5, preferably from 5.5 to 8, in particular at neutral pH, for example, at pH 6–7.5, at from 50 to 100° C., in particular from 70 to 100° C., in the case of atmospheric pressure and at from 100 to 250° C., preferably from 100 to 200° C., in the case of hydrothermal conditions.

Pure hemimorphite having a Zn/Si ratio of 2 can be synthesized by this preparation method. However, hemimorphite preparation having a zinc content up to 25% less than or greater than the stoichiometric amount, corresponding to a Zn : Si atomic ratio of from 1.6 to 2.5, are also obtainable. Hemimorphites which contain 0–20% excess of zinc are preferred as catalysts. Hemimorphites which contain 0–10% excess of zinc are particularly preferred.

The hemimorphite products are obtained in the synthesis as white crystalline precipitate in the form of an aqueous suspension and must be separated from the aqueous solution by suitable measures, for example filtration or centrifuging. In the case of filtration, the filter cake obtained is then washed sodium- and nitrate-free and then dried. Drying can be carried out at up to 600° C., preferably from 90 to 250° C. Thermogravimetric investigations have shown that the crystallized hemimorphite of the composition $Zn_4Si_2O_7$ $(OH)_2 \cdot H_2O$ loses increasing proportions of its water of crystallization at from about 100 to 200° C. with a retention of the hemimorphite structure, resulting in hemimorphite preparations of the composition $Zn_4Si_2O_7(OH)_2 \cdot x\ H_2O$ where x is less than 1 and decreases with increasing temperature. If drying is carried out in a higher temperature range from about 200 to 600° C., the $OH^-$ ions present in the hemimorphite are additionally converted into $O^{2-}$-ions and eliminated $H_2O$ ($2\ OH^- \rightarrow H_2O + O^{2-}$), likewise with retention of the hemimorphite structure, resulting in hemimorphite preparations of the composition $Zn_4Si_2O_7(OH)_{2-2y}O_y$, where y is from 0 to 1 and increases with increasing temperature.

Hemimorphite preparations obtained after drying up to 600° C., preferably from 90 to 450° C., and having the composition $Zn_4Si_2O_7(OH)_{2-2y}O_y \cdot x\ H_2O$, where x and y are from 0 to 1, are then usually processed by the conventional shaping methods, for example pelleting or extrusion, or are converted into coated catalysts on steatite beads to give catalytic moldings. The details are described in the examples.

Standard methods are used for characterizing the catalyst samples (fresh samples as well as samples removed from the reactor). The measured BET surface area is as a rule from 3 to 400 $m^2/g$. Catalysts with BET surface areas of from 20 to 300 $m^2/g$ are preferably used. Furthermore, the samples obtained by the novel preparation process are investigated in detail by means of powder X-ray diffractometry (XRD) and transmission electron microscopy (TEM). The measured powder X-ray diffraction pattern agrees with that of index card 5–0555 of the JCPDS-ICDD index (1995).

(c) X-ray amorphous zinc silicate catalyst

If the procedure is carried out essentially under the same preparation conditions but for a shorter reaction time, an X-ray amorphous product having improved catalytic properties is obtained as an intermediate for the preparation of a crystalline hemimorphite.

For this purpose, an aqueous suspension of an alkali metal or alkaline earth metal silicate is reacted with an aqueous solution of a zinc salt a) at from 20° C., preferably 50° C., to the boiling point of the resulting aqueous suspension b) at a pH of from 4 to 9.5, preferably at a pH close to the neutral point, c) and in ratios of alkali metal silicate to zinc salt such that the conditions of the formula V are fulfilled and d) the residence time is maintained such that crystallization of the zinc silicate does not yet occur to any considerable extent.

The essentially X-ray amorphous zinc silicate thus obtainable contains $Zn^{2+-}$, $Si^{4+}$ and $O^{2-}$ ions; in addition, the compound may contain OH ions and water of hydration. The Zn/Si ratio is from 0.3 to 5, preferably from 1 to 2.7, particularly preferably from 2 to 2.3, very particularly preferably 2. In the latter case, the X-ray amorphous zinc silicate thus has the Zn/Si ratio of crystalline hemimorphite $(Zn_4Si_2O_7(OH)_2 \cdot H_2O)$. In a graph in which the intensity A of the diffracted X-rays is plotted as a function of twice the diffraction angle ($2\theta$), the powder X-ray diffraction pattern of the X-ray amorphous zinc silicate, obtained using Cu-$K\alpha_1$ radiation ($\gamma=1.5406$ Å), has, in the $2\theta$ range from 10 to 90°, very broad intensity maxima at $2\theta=31°\pm5°$ and at $2\theta=61°\pm7°$.

The precipitated amorphous zinc silicate catalyst to be used according to the invention can also be doped with up to 80, preferably up to 50, in particular up to 20, mol percent of further metals selected from the group (A) consisting of beryllium, magnesium, calcium, strontium, barium, manganese, iron, cobalt, nickel, copper, cadmium and mercury and from the group (B), consisting of titanium, zirconium, hafnium, germanium, tin and lead, the elements of group (A) replacing some of the zinc and the elements of group (B) replacing some of the silicon in the hemimorphite structure.

The X-ray amorphous zinc silicate is obtained as a powder in the preparation. This powder can be used as such for the catalytic reaction (for example in a fluidized-bed reactor) or after molding (for example extrusion, pelleting, etc., possibly also with the addition of assistants in a form suitable for a fixed-bed reactor.

Before use, the catalyst can be calcined at from 80 to 750° C., preferably from 120 to 500° C., particularly preferably from 200 to 400° C. in the air. To increase the pore volume, pore formers may also be added during the shaping, for example during the pelleting or extrusion (for example superabsorbers such as Lutexal P® (from BASF AG) or Walocel® (methylcellulose/synthetic resin combination, from Wolff, Walsrode AG)).

General reaction conditions of the novel combination process with the steps (a), (b) and (c).

The combination of stages (a) to (c) can be carried out batchwise or, preferably, continuously. In the case of the batchwise procedure, the ketal of the formula IV obtained as a byproduct in stage (a) is collected in a storage container and converted into the enol ether of the formula III, temporarily, and, if required, spatially separately from the process of stage (a). In the continuous procedure preferred on the industrial scale, the preparation of the enol ether and the recycling of the ketal to the enol ether preparation stage are spatially integrated in one plant. A very small volume is then required for the buffer container and transport is dispensed with.

The reaction of stage (b) is carried out as a rule in a tube reactor, the propyne and/or allene (or preferably a mixture composed of 30–43% by volume of propyne, 16–20% by volume of allene, 20–45% by volume of propene, 5–10 by volume of isobutane and 2–6% by volume of propane, obtained by distillation from a side-stream of a steam cracker) were metered in with the ketal under superatmospheric pressure. The starting materials are mixed shortly before the reactor and are let down into the reactor space.

The reaction is carried out as a rule isothermally from 120 to 300° C. and with a feed rate of from 0.5 to 10 mmol/min of propyne and/or allene and from 0.5 to 20 mmol/min of ketal. The reaction pressure is from 0.1 to 50, preferably from 1.1 to 3.5, bar (absolute).

The enol ether formed in stage (b) is separated from the propene/propane inert gas stream and then purified by distillation. The distilled enol ether is then used in stage (a).

The ketal formed as a byproduct in stage (a) is separated from the reacted mixture, if necessary after prior neutralization, by distillation over a column having about 10 theoretical plates at from 100 mbar to 1 bar, preferably from 300 to 800 mbar, and is taken off via the top. The distillate contains excess enol ether III and acetone in addition to the ketal IV. This stream can, in accordance with stage (c), be fed directly into the synthesis of the enol ether or, preferably, be further purified in another column. This column can be operated batchwise or, preferably, continuously. In this case, the excess enol ether III is obtained as top product and used directly as a starting material for stage (a). Acetone is removed via a side take-off. The ketal IV is obtained at the bottom and is reacted with propyne/allene to give the enol ether III, in accordance with stage (c).

EXAMPLES

Example 1

Stage a)

200 g of hydrodehydrolinalool (1.3 mol), 306 g of an azeotropic mixture consisting of 2-methoxypropene (prepared by the process of stage b, see below) and methanol (3.9 mol of 2-methoxypropene) and 1 g of potassium hydrogen sulfate (dried and powdered) were introduced into a pressure-resistant vessel. The reactor was flushed with nitrogen and closed. The reaction was initiated during heating up. The temperature increased to 140° C. in the course of about 20 minutes, and the pressure to about 5 bar. The reaction mixture was then stirred for a further 2.5 hours at 120° C. to complete the reaction. First, the low boilers contained in the reacted mixture, ie. primarily 2,2-dimethoxypropane and excess 2-methoxypropene, were separated off in a rotary evaporator at about 500 mbar and condensed in a cold trap. The residue was distilled at a reduced pressure of 1 mbar over a bridge. 249 g of 6,10-dimethylundeca-4,5-dien-2-one were obtained in a purity of 85%.

Stage c)

The condensate containing 2,2-dimethoxypropane, acetone and excess 2-methoxypropene and obtained from a plurality of batches were subjected to fractional distillation and the fraction consisting of 2-methoxypropene was reused directly for stage (a). The fraction consisting of 2,2-dimethoxypropane was fed into stage (b). The fraction consisting mainly of acetone was discarded.

Stage b)

ba) Preparation of the catalyst (amorphous zinc silicate; by impregnation)

The $Zn/SiO_2$ supported catalyst was obtained by impregnating X-ray amorphous $SiO_2$ moldings (beads of diameter 3–6 mm) having a BET surface area of 358 $m^2/g$, a water absorbtivity of 0.9 ml/g and a hardness of 43 N/molding with ammoniacal zinc acetate solution. For this purpose, 225 g of $SiO_2$ carrier (Siligel, from Solvay) were impregnated with 151.70 g of $Zn(OAc)_2 \cdot 2 H_2O$ (Merck), dissolved in 220 g of 9% strength $NH_4OH$ solution at room temperature, and the precatalyst was dried for 16 hours at 120° C. and then calcined for 4 hours under air at 250° C. The precatalyst had a BET surface area of 195 $m^2/g$ and a hardness of 76 N/molding. The acetate/Zn ratio was 0.9 mol/mol.

bb) Reaction

About 90 ml of precatalyst were introduced into a stirred reactor. Propyne/allene mixture (55 mol %, remainder propene) and 2,2-dimethoxypropane were then metered in by means of HPLC pumps. The reaction was continued at the first setting (170° C.) until the active catalyst had completely formed and the conversion and selectivity were constant (about 20 hours). The temperature and the feeds were then changed according to Table 1. The results are summarized in Table 1. The pressure was 1.35 bar (abs) in all experiments. Abbreviations: 2 MP: 2-methoxypropene; 22 DMP: 2,2-dimethoxypropane; 1 MP: 1-methoxypropene (cis and trans); 11 DMP: 1,1-dimethoxypropane. The stated selectivities are based on propyne and allene.

The condensed reacted mixtures were subjected to fractional distillation. The 2-methoxypropene fraction was used as a starting material in stage (a) and the unconverted dimethoxypropane fraction was recycled to reaction (bb).

TABLE 1

| | | Feeds/mmol/min | | | Conversions/% | | Selectivities/% | | | |
|---|---|---|---|---|---|---|---|---|---|---|
| Exp. No. | Temp. °C. | Propyne/ Allene | 22DMP | Total | Propyne/ Allene | 22DMP | 2MP | Acetone | 1MP | 11DMP |
| 1.1 | 170 | 2.31 | 2.17 | 6.20 | 69 | 90 | 95 | 1 | 2 | <1 |
| 1.2 | 150 | 1.36 | 1.57 | 4.26 | 57 | 69 | 96 | 1 | 2 | <1 |
| 1.3 | 130 | 1.13 | 1.11 | 3.31 | 44 | 59 | 96 | 1 | 2 | <1 |

Example 2

Stage a)

190 g of 3,7,11-trimethyldodec-1-yn-3-ol (purity 95%, 0.848 mol) and 200 g of 2-methoxypropene (2.78 mol) and 0.58 g of $KHSO_4$, dissolved in 1.74 g of water, were introduced into a pressure-resistant vessel. The reactor was flushed with nitrogen and closed. After a reaction time of 1 hour at 120° C., the mixture was cooled to about 50° C. and a further 0.58 g of $KHSO_4$, dissolved in 1.74 g of water, was added. The mixture was once again heated to 120° C. After a reaction time of one hour, the reaction was complete. Distillation was carried out as in Example 1.147 g of a mixture comprising mainly 2-methoxypropene and 2,2-dimethoxypropane and 213 g of a fraction comprising 1.6% of 3,7,11-trimethyldodec-1-yn-3-ol, 67% of 6,10,14-trimethylpentadeca-4,5-dien-2-one, and 7.3% of 6,10,14-trimethylpentadeca-3,5-dien-2-one were obtained.

Stage c)

The methoxypropene/2,2-dimethoxypropane/acetone mixture from a plurality of batches was subjected to fractional distillation, the methoxypropene fraction was reused directly for the reaction of stage (a) and the dimethoxypropane fraction was introduced into stage b (see below) as a starting material.

Stage b)

ba) Preparation of the catalyst (hemimorphite Zn/Si=2)

In an 8 l stirred container, a suspension A comprising 1.5 mol of $SiO_2$ and 0.89 mol of Na was prepared from 4.5 l of demineralized water and 145.1 g of soda water glass powder containing 62.1% by weight of $SiO_2$ and 19.0% by weight of $Na_2O$ (from Riedel-de Haen, D-30918 Seelze). Furthermore, 910.7 g of $Zn(NO_3)_2 \cdot 6\,H_2O$ (98% strength) were dissolved in 2.25 l of demineralized water at room temperature, a solution B containing 3 mol of Zn and 6 mol of $NO_3$ being obtained. Finally, an aqueous solution was prepared from 204.4 g of NaOH in 0.225 l of demineralized water, a solution C having an Na content of 5.11 mol being obtained. Solutions B and C were then added to suspension A at room temperature, a milky suspension D containing the following proportions of elements being obtained: Zn content=3 mol, Si content=1.5 mol, Na content=6 mol, $NO_3$ content=6 mol. The pH of the resulting suspension D was 7.1. The suspension D was heated to 90° C. and stirred at a speed of 200 rpm for 24 hours at this temperature. The suspension was then cooled to room temperature, and a final pH of 7.0 was measured. The white precipitate which crystallized out was filtered off and washed Na-free with demineralized water and the resulting filter cake was dried at 90° C. in a drying oven.

The dried white powder was investigated by X-ray diffraction and gave an X-ray powder pattern which corresponded completely to index card 5–0555 of the JCPDS-ICDD index (1995) and thus indicated the preparation of $Zn_4Si_2O_7(OH)_2 \cdot H_2O$. The specific surface area of the resulting powder, determined according to BET, was 30 m²/g.

For the preparation of a catalyst, the still moist powder was directly molded to give extrudates (diameter=3 mm, pressure=50 bar), which were then dried for 16 hours at 120° C. The prepared catalyst had a BET surface area of 26 m²/g and a hardness of 6 N/molding.

bb) Reaction

About 90 ml of the catalyst were introduced into a stirred reactor. Propyne/allene (about 63% strength by volume, 1.68 mmol/min) and 2,2-dimethoxypropane (2.17 mmol/min; total feed with inert substances: 6.46 mmol/min; 2,2-dimethoxypropane/(propyne+allene) ratio=1.29) were then metered in by means of HPLC pumps. The reaction temperature was 170° C. and the pressure 1.35 bar (abs), and the partial pressure of the starting materials was 0.8 bar. The following selectivities were observed from the beginning (ie. the catalyst had no forming time): 2-methoxypropene: 97.4%; acetone: 2.3%; cis- and trans-1-methoxypropene: 0.3%.

The condensed reacted mixtures were subjected to fractional distillation. The 2-methoxypropene fraction was used as a starting material in stage (a) and the dimethoxypropane fraction not added was recycled to the reaction (bb). By-products formed in small amounts were discarded.

Example 3

Stage a)

25.9 g of hydrolinalool and 45.5 g of isopropenyl ethyl ether (purity 85%) and 93 mg of 75% strength phosphoric acid were introduced into a pressure-resistant container having a volume of 300 ml, and the container was closed, flushed with nitrogen and heated to 175° C. After a reaction time of 12 hours, the container was cooled and emptied and the reacted mixture was distilled over a column (h=10 cm, filled with 3 mm wire mesh rings). The first fraction (27.2 g) distilled over at 70° C. at atmospheric pressure and contained 2,2-diethoxypropane as the main product. At 0.9 mbar, 6,10-dimethylundec-5-en-2-one was obtained in a yield of 83%.

Stage c)

The forerun containing 2,2-diethoxypropane was collected from a plurality of batches and introduced into stage b) as starting material.

Stage b)

ba) Preparation of the catalyst (hemimorphite Zn/Si=2.2)

In a 6 l stirred container, a suspension A containing 1.0 mol of $SiO_2$ and 0.59 mol of Na was prepared from 3.0 l of demineralized water and 96.8 g of soda water glass powder containing 62.1% by weight of $SiO_2$ and 19.0% by weight of $Na_2O$ (from Riedel-de Haen, D-30918 Seelze), a solution B containing 2.2 mol of Zn and 4.4 mol of $NO_3$ was prepared from 667.8 g of $Zn(NO_3)_2 \cdot 6\,H_2O$ (98% strength) in 1.5 l of demineralized water at room temperature and an aqueous solution C having an Na content of 3.81 mol was prepared from 152.3 g of NaOH in 0.4 l of demineralized water. Solutions B and C were added to suspension A at room temperature, a milky suspension D containing the following proportions of elements being obtained: Zn content=2.2 mol, Si content=1 mol, Na content=4.4 mol, $NO_3$ content=4.4 mol. The pH of the resulting suspension D was 7.2. The suspension D was heated to 90° C. and stirred at 200 rpm for 24 hours at this temperature. After the suspension had been cooled to room temperature, a final pH of 7.0 was measured. The resulting white precipitate was filtered off and washed Na-free with demineralized water and the filter cake obtained was dried at 90° C. in a drying oven.

The dried white powder was investigated by X-ray diffraction and gave an X-ray powder pattern which completely corresponded to index card 5–0555 of the JCPDS-ICDD index (1995) and thus indicated the preparation of $Zn_4Si_2O_7(OH)_2 \cdot H_2O$. The specific surface area of the resulting powder, determined according to BET, was 60 m²/g.

650 g of the powder were mixed with 20.2 g of magnesium stearate (Merck) and molded to give 20 mm pellets. These pellets were processed to give chips (<0.5 mm). The pellets were then calcined for 10 hours at 350° C. The prepared catalyst had a BET surface area of 44 m²/g and a hardness of 44 N/molding.

bb) Reaction

About 90 ml of the catalyst were introduced into a stirred reactor. Propyne/allene mixture (about 60% strength by volume, 1.64 mmol/min) and 2,2-diethoxypropane (2.14 mmol/min; total feed with inert substances: 8.34 mmol/min; 2,2-diethoxypropane/(propyne+allene) ratio=1.30) were then metered in by means of HPLC pumps. The reaction temperature was 170° C. and the pressure 1.35 bar (abs.), and the partial pressure of the starting materials was 0.8 bar. The following selectivities were observed from the beginning (ie. the catalyst had no forming time): 2-ethoxypropene: 97.0%; acetone: 2.3%; cis- and trans-1-ethoxypropene: 0.5%.

The following values were determined for the catalyst after removal from the reactor: BET surface area 44 m²/g, hardness 12 N/molding.

The collected condensed reacted mixture was subjected to fractional distillation and the 2-ethoxypropene fraction was fed to stage a) as a starting material. Unconverted diethoxypropane was recycled to the reaction.

Example 4

Stage a)

18.7 g of hydrolinalool, 46 g of isopropenyl propyl ether (purity 80%) and 85 mg of 75% strength phosphoric acid were reacted and worked up as in the previous example. 27 g of a byproduct fraction containing 2,2-dipropoxypropane as the main component and a yield of 79% of theory, based on hydrolinalool, of 6,10-dimethylundec-5-en-2-one were obtained.

The 2,2-dipropoxypropane fraction was fed to stage (b).

Stage b)

(Precipitated X-ray amorphous catalyst; Zn/Si ratio 2.1)

In a 12 l stirred container, 120.93 g of soda water glass powder containing 62.1% by weight of $SiO_2$ and 19.0% by weight of $Na_2O$ (from Riedel-de-Haen, D-30918 Seelze) were added to 7.5 l of demineralized water at 80° C with constant stirring (100 rpm), a suspension A containing 1.25 mol of $SiO_2$ and 0.74 mol of Na being obtained. An aqueous solution B comprising 180.4 g of NaOH (corresponding to 4.51 mol of Na) in 0.5 l of demineralized water was then prepared. In addition, 796.8 g of $Zn(NO_3)_2 \cdot 6\ H_2O$ (Zn content=98%) were dissolved in 2.5 l of demineralized water, a solution C containing 2.625 mol of Zn and 5.25 mol of $NO_3$ being obtained. The solution B was then added to the suspension A at 80° C., a clear solution D being obtained after about 5 minutes. The solution C was then added to the solution D obtained. A white suspension E containing 2.625 mol of Zn, 1.25 mol of Si, 5.25 mol of Na and 5.25 mol of $NO_3$ resulted. The suspension E was heated at 80° C. for 2 hours while stirring (100 rpm) and then cooled to room temperature. After cooling, a final pH of 6.5 was measured. The resulting white precipitate was filtered off and washed Na-free with demineralized water. The filter cake obtained was dried at 80° C. in a drying oven.

BRIEF DESCRIPTION OF THE DRAWINGS

The dried white powder was investigated by X-ray diffraction and gave an X-ray powder pattern which corresponded to that of FIG. 1 and thus indicated the preparation of predominant amounts of X-ray amorphous zinc silicate in addition to a small amount of crystalline ZnO (index card 5–0664 of the JCPDS-ICDD index (1995)). The specific surface area of the resulting powder, determined according to BET, was 102.1 m²/g.

650 g of the amorphous zinc silicate prepared as described above and having the composition of hemimorphite were mixed with 20.2 g of zinc stearate and precompacted to give 20 mm pellet, then communicated to chips having a diameter of <0.5 mm and then molded to give pellets measuring 4.75×5.2 mm. The catalyst had a BET surface area of 75 m²/g and a hardness of 43 N/pellet. A 100 g portion of the catalyst was then calcined at 350° C. for 10 hours in the air.

Figure 1:
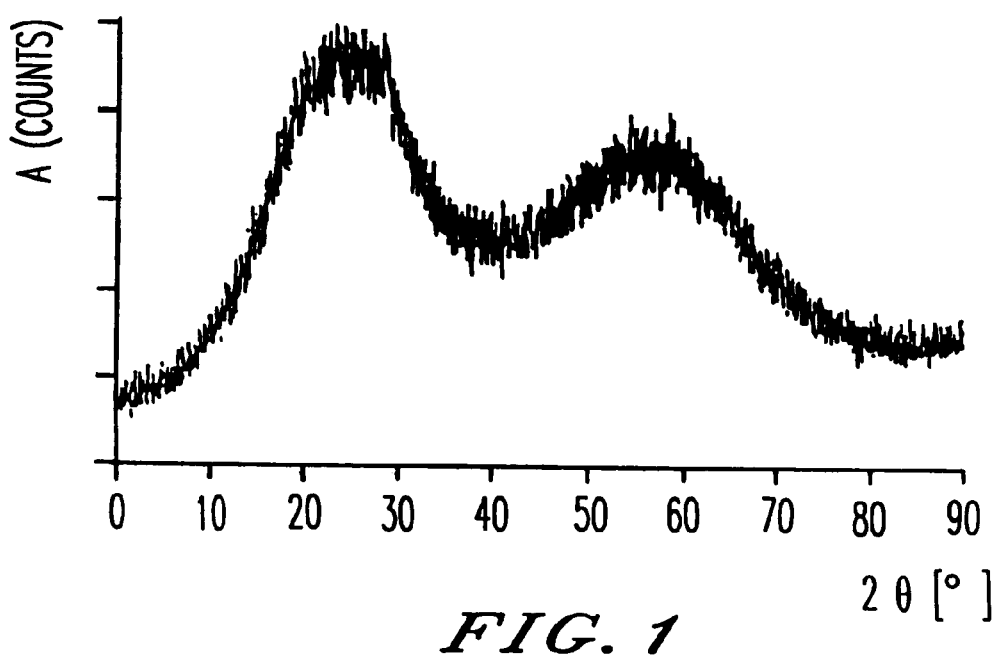

About 90 ml of the catalyst were introduced into a stirred reactor. Propyne/allene mixture (49.8% strength by volume, 1.84 mmol/min) and 2,2-dipropoxypropane (2.15 mmol/min; total feed with inert substances: 6.79 mmol/min; 2,2-dipropoxypropane/(propyne+allene) ratio=1.17) were then metered in by means of HPLC pumps. The reaction temperature was 170° C. and the pressure 1.35 bar (abs), and the partial pressure of the starting materials was 0.8 bar. The following selectivities were observed: 2-propoxypropene 97.1%; 2-dipropoxypropane 2.5%; cis- and trans-1-propoxypropene 0.4%. The conversion was 21%, based on propyne/propadiene.

This catalyst had virtually no forming time. The stated conversion and the selectivity were virtually constant from the beginning. The BET surface area was 82 m²/g after the calcination and 64 m²/g after removal from the reactor. The hardness was 28 N/pellet after calcination and 36 N/pellet after removal from the reactor.

Example 5

380.8 g of hydrolinalool, 55.5 g of isopropenyl n-butyl ether (purity 90%) and 113 mg of 75% strength phosphoric acid were reacted as in Example 4. Working up was carried out by distillation at 0.3 mbar. 29 g of a mixture consisting mainly of 2,2-dibutoxypropane, isopropenyl n-butyl ether and butanol were obtained and 6,10-dimethylundec-5-en-2-one was obtained in a yield of 74%.

Using the catalyst described in Example 4, similar results were obtained on recycling of the 2,2-dibutoxypropane and reaction with fresh 2,2-dibutoxypropane.

Example 6

66 g of hydronerolidol, 60 g of an azeotropic mixture of isopropenyl methyl ether and methanol (about 91% of isopropenyl methyl ether) and 248 mg of 75% strength phosphoric acid were combined in a pressure-resistant vessel. After flushing with nitrogen, the reaction mixture was stirred for 8 hours at 150° C. The reacted mixture was neutralized with aluminum triisopropylate and subjected to fractional distillation. 42 g of a mixture comprising 85% of 2,2-dimethoxypropane, 11.3% of acetone, 0.4% of isopropenyl methyl ether and 0.4% of methanol were obtained at atmospheric pressure. At 0.3 mbar, 6,10,14-trimethylpentadeca-5,9-dien-2-one was obtained in a yield of 78%, based on hydronerolidol used.

Similar results were obtained if the preparation of the 2-methoxypropene is carried out as described in Example 1 and the 2,2-dimethoxypropane obtained as a byproduct is separated from acetone and then recycled to stage (b).

We claim:

1. A process for the preparation of unsaturated ketones of the formulae Ia and Ib

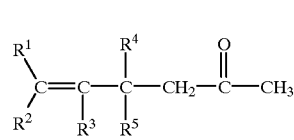

Ia

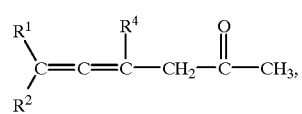

Ib where $R^1$, $R^2$, $R^3$, $R^4$ and $R^5$ are each hydrogen or alkyl, alkenyl, cycloalkyl, cycloalkenyl, aryl or aralkyl radicals which are substituted or unsubstituted by oxygen-containing groups, it also being possible for $R^1$ and $R^2$ together to form a 5- or 6-membered carboxylic ring, which comprises the combination of the following reactions:

a) reacting an allyl alcohol of the formula IIa or a propargyl alcohol of the formula IIb

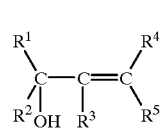

IIa

-continued

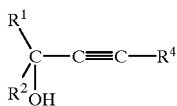
IIb with an isopropenyl ether of the formula III

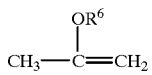
III where $R^6$ is alkyl having 1 to 4 carbon atoms, with formation of a ketal of the formula IV

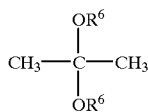
IV where $R^6$ has the abovementioned meaning, as a byproduct,
b) preparation of the isopropenyl ether of the formula III by reacting a ketal of the formula IV with propyne or allene, and a mixture thereof in the gas phase at elevated temperatures in the presence of a heterogeneous catalyst containing zinc or cadmium together with silicon or oxygen, and
c) feeding the ketal of the formula IV formed in the reaction (a) into stage (b) for the preparation of the isopropenyl ether of the formula III again.

2. The process as claimed in claim 1, wherein a compound of the formula IIa selected from the group consisting of 3-methyl-1-buten-3-ol, 3,7-dimethyl-1-octen-3-ol, 3,7-dimethylocta-2,6-dien-3-ol, 1-vinylcyclohexanol, 3,7,11-trimethyldodeca-1,6,10-trien-3-ol and 3,7,11-trimethyldodec-1-en-3-ol is reacted with isopropenyl methyl ether, which is prepared by reacting fresh and recycled acetone dimethyl ketal with propyne and/or allene in the gas phase at elevated temperatures in the presence of a zinc silicate catalyst.

3. The process as claimed in claim 1, wherein a compound of the formula IIb selected from the group consisting of 3-methylbutyn-3-ol, 3,7-dimethyl-1-octyn-3-ol, 3,7-dimethylocta-6-en-1-yn-3-ol, 3,7,11-trimethyldodeca-6,10-dien-1-yn-3-ol, 3,7,11-trimethyldodeca-6-en-1-yn-3-ol and 3,7,11-trimethyldodec-1-yn-3-ol is reacted with isopropenyl methyl ether, which is prepared by reacting fresh or recycled acetone dimethyl ketal with propyne or allene in the gas phase at elevated temperatures in the presence of a zinc silicate catalyst.

4. The process as claimed in claim 1, wherein the reaction of stage (b) is carried out in the presence of a catalyst which has a BET surface area of from 10 to 800 m$^2$/g.

5. The process as claimed in claim 1, wherein the catalyst used for stage (b) is an X-ray amorphous zinc silicate obtainable by applying a zinc salt to amorphous silica and forming the catalyst at from 50 to 400° C.

6. The process as claimed in claim 1, wherein the catalyst used for stage (b) is a zinc silicate having the hemimorphite structure of formula $Zn_4Si_2O_7(OH)_{2-2y}O_y \cdot xH_2O$, where x and y are from 0 to 1.

7. The process as claimed in claim 1, wherein the catalyst used for stage (b) is an X-ray amorphous zinc silicate of formula V $$Zn_aSi_cO_{a+2c-0.5e}(OH)_e \cdot f H_2O \quad V$$

where e is from 0 to 2a+4c and the ratio a/c is from 1 to 3.5 and the ratio f/a is from 0 to 200, obtainable by precipitation in aqueous solution.

8. The process as claimed in claim 1, wherein the reaction of stage (b) is carried out at from 50 to 400° C. and from 0.1 to 50 bar.

9. The process as claimed in claim 1, which is carried out continuously.

* * * * *